(12) United States Patent
Kern et al.

(10) Patent No.: US 11,744,991 B2
(45) Date of Patent: *Sep. 5, 2023

(54) COMPOUND CURVE NAVIGATION CATHETER

(71) Applicant: Covidien LP, Mansfield, MA (US)

(72) Inventors: Michael J. Kern, Minnetonka, MN (US); Michael E. Calcutt, Burnsville, MN (US)

(73) Assignee: Covidien LP, Mansfield, MA (US)

(*) Notice: Subject to any disclaimer, the term of this patent is extended or adjusted under 35 U.S.C. 154(b) by 650 days.

This patent is subject to a terminal disclaimer.

(21) Appl. No.: 16/788,562

(22) Filed: Feb. 12, 2020

(65) Prior Publication Data
US 2020/0179649 A1    Jun. 11, 2020

Related U.S. Application Data

(63) Continuation of application No. 15/069,214, filed on Mar. 14, 2016, now Pat. No. 10,583,270.

(51) Int. Cl.
*A61M 25/01* (2006.01)
*A61M 25/00* (2006.01)
(Continued)

(52) U.S. Cl.
CPC .... *A61M 25/0136* (2013.01); *A61M 25/0009* (2013.01); *A61M 25/0021* (2013.01);
(Continued)

(58) Field of Classification Search
CPC .. A61M 2025/0046; A61M 2025/0166; A61M 2025/09175; A61M 2210/103;
(Continued)

(56) References Cited

U.S. PATENT DOCUMENTS 4,735,620 A    4/1988 Ruiz
5,624,397 A    4/1997 Snoke et al.
(Continued)

FOREIGN PATENT DOCUMENTS

CN    104605932 A    5/2015
EP    2135634 A1    12/2009
(Continued)

OTHER PUBLICATIONS

Australian Examination Report No. 1, dated Feb. 3, 2018, corresponding to Australian Application No. 2017201191; 10 pages.
(Continued)

*Primary Examiner* — Brandy S Lee
(74) *Attorney, Agent, or Firm* — Carter, DeLuca & Farrell LLP

(57) ABSTRACT

A catheter assembly for navigation including a flexible catheter having a proximal portion adjacent a proximal end and a distal portion adjacent a distal end and defining a longitudinal axis, the flexible catheter defining a lumen extending therethrough along a longitudinal axis and configured to enable translation of an instrument from the proximal end to the distal end. The flexible catheter defines a compound curve formed on the distal portion, wherein the compound curve includes an elbow bend and a radially curved portion. The elbow bend deflecting the distal portion of the flexible catheter from the longitudinal axis, while the radially curved portion extends from the elbow bend farther deflecting the distal portion about a center point. The catheter guide assembly for navigation includes a control handle disposed at the proximal end of the flexible catheter and is configured to advance and rotate the flexible catheter within a luminal structure.

18 Claims, 9 Drawing Sheets

(51) Int. Cl.
*A61M 25/09* (2006.01)
*B29C 65/56* (2006.01)
*B29D 23/00* (2006.01)
*A61B 34/20* (2016.01)
*A61B 10/02* (2006.01)
*A61B 10/04* (2006.01)
*A61B 10/06* (2006.01)
*A61B 18/00* (2006.01)
*B29L 31/00* (2006.01)

(52) U.S. Cl.
CPC ........ *A61M 25/0067* (2013.01); *A61M 25/09* (2013.01); *B29C 65/56* (2013.01); *B29D 23/00* (2013.01); *A61B 10/0283* (2013.01); *A61B 10/06* (2013.01); *A61B 18/00* (2013.01); *A61B 2010/0216* (2013.01); *A61B 2010/045* (2013.01); *A61B 2034/2051* (2016.02); *A61M 25/0041* (2013.01); *A61M 25/0054* (2013.01); *A61M 2025/0046* (2013.01); *A61M 2025/0166* (2013.01); *A61M 2025/09175* (2013.01); *A61M 2210/1035* (2013.01); *A61M 2210/1039* (2013.01); *B29L 2031/7542* (2013.01)

(58) Field of Classification Search
CPC ...... A61M 2210/1039; A61M 25/0009; A61M 25/0021; A61M 25/0041; A61M 25/0054; A61M 25/0067; A61M 25/0136; A61M 25/09; A61M 2210/1035; A61B 10/0283; A61B 10/06; A61B 18/00; A61B 2010/0216; A61B 2010/045; A61B 2034/2051; B29C 65/56
See application file for complete search history.

(56) References Cited

U.S. PATENT DOCUMENTS

| | | | |
|---|---|---|---|
| 5,779,646 A | 7/1998 | Koblish et al. | |
| 5,964,727 A | 10/1999 | Edwards et al. | |
| 6,592,581 B2 | 7/2003 | Bowe | |
| 6,605,086 B2 | 8/2003 | Hayzelden et al. | |
| 6,648,875 B2 | 11/2003 | Simpson et al. | |
| 6,652,517 B1 | 11/2003 | Hall et al. | |
| 7,090,683 B2 | 8/2006 | Brock et al. | |
| 7,395,116 B2 | 7/2008 | Mehdizadeh et al. | |
| 7,608,056 B2 | 10/2009 | Kennedy, II | |
| 7,678,117 B2 | 3/2010 | Hinman et al. | |
| 7,998,112 B2 | 8/2011 | Chow et al. | |
| 8,568,390 B2 | 10/2013 | Mueller | |
| 10,583,270 B2 | 3/2020 | Kern et al. | |
| 2003/0135204 A1 | 7/2003 | Lee et al. | |
| 2003/0144657 A1* | 7/2003 | Bowe ................ | A61M 25/0133 606/41 |
| 2004/0073158 A1 | 4/2004 | Shah et al. | |
| 2006/0074383 A1 | 4/2006 | Boulais | |
| 2006/0178556 A1 | 8/2006 | Hasser et al. | |
| 2006/0199999 A1 | 9/2006 | Ikeda et al. | |
| 2007/0066878 A1 | 3/2007 | Worley et al. | |
| 2007/0100235 A1 | 5/2007 | Kennedy | |
| 2007/0219550 A1 | 9/2007 | Thompson et al. | |
| 2007/0244473 A1 | 10/2007 | Thompson et al. | |
| 2007/0282358 A1 | 12/2007 | Remiszewski | |
| 2007/0293721 A1* | 12/2007 | Gilboa ................ | A61B 5/065 600/117 |
| 2010/0022948 A1 | 1/2010 | Wilson et al. | |
| 2010/0217261 A1 | 8/2010 | Watson | |
| 2010/0241155 A1 | 9/2010 | Chang et al. | |
| 2012/0109178 A1 | 5/2012 | Edwards et al. | |
| 2013/0023924 A1 | 1/2013 | Mueller | |
| 2013/0184598 A1 | 7/2013 | Bowe et al. | |
| 2014/0261407 A1 | 9/2014 | Roberts et al. | |
| 2014/0270441 A1 | 9/2014 | Baker | |
| 2014/0350458 A1 | 11/2014 | Roberts et al. | |
| 2015/0045776 A1 | 2/2015 | Haac | |
| 2015/0126852 A1 | 5/2015 | Costello | |
| 2016/0000302 A1 | 1/2016 | Brown et al. | |
| 2016/0000356 A1 | 1/2016 | Brown et al. | |
| 2016/0008061 A1 | 1/2016 | Fung et al. | |
| 2017/0259037 A1 | 9/2017 | Kern et al. | |

FOREIGN PATENT DOCUMENTS

| | | |
|---|---|---|
| EP | 2868340 A1 | 5/2015 |
| EP | 3219351 A1 | 9/2017 |
| JP | 2011000389 A | 1/2011 |
| JP | 2015066331 A | 4/2015 |
| JP | 2015085197 A | 5/2015 |
| WO | 2005035043 A2 | 4/2005 |

OTHER PUBLICATIONS

Japanese Office Action (with English translation) dated Jan. 31, 2018, corresponding to Japanese Application No. 2017-046148; 9 total pages.
Extended European Search Report issued in corresponding application No. 17159909.5 dated Aug. 18, 2017.
Canadian Office Action and Examination Search Report dated Dec. 27, 2018, corresponding to Canadian Application No. 2,959,925; 4 total pages.
Japanese Office Action (with English translation), dated Jun. 5, 2018, corresponding to Japanese Application No. 2017-046148; 7 total pages.
Canadian Office Action and Examination Search Report dated Jul. 16, 2018, corresponding to Canadian Application No. 2,959,925; 4 total pages.
Chinese Office Action and Search Report with English translation, dated Apr. 16, 2019, corresponding to counterpart Chinese Application No. 201710149228.0; 13 total pages.
Canadian Office Action and Examination Search Report dated Jan. 26, 2018, corresponding to Canadian Application No. 2,959,925; 4 total pages.
European examination report issued in corresponding application EP 17159909.5 dated Mar. 26, 2021 (4 pages).

* cited by examiner

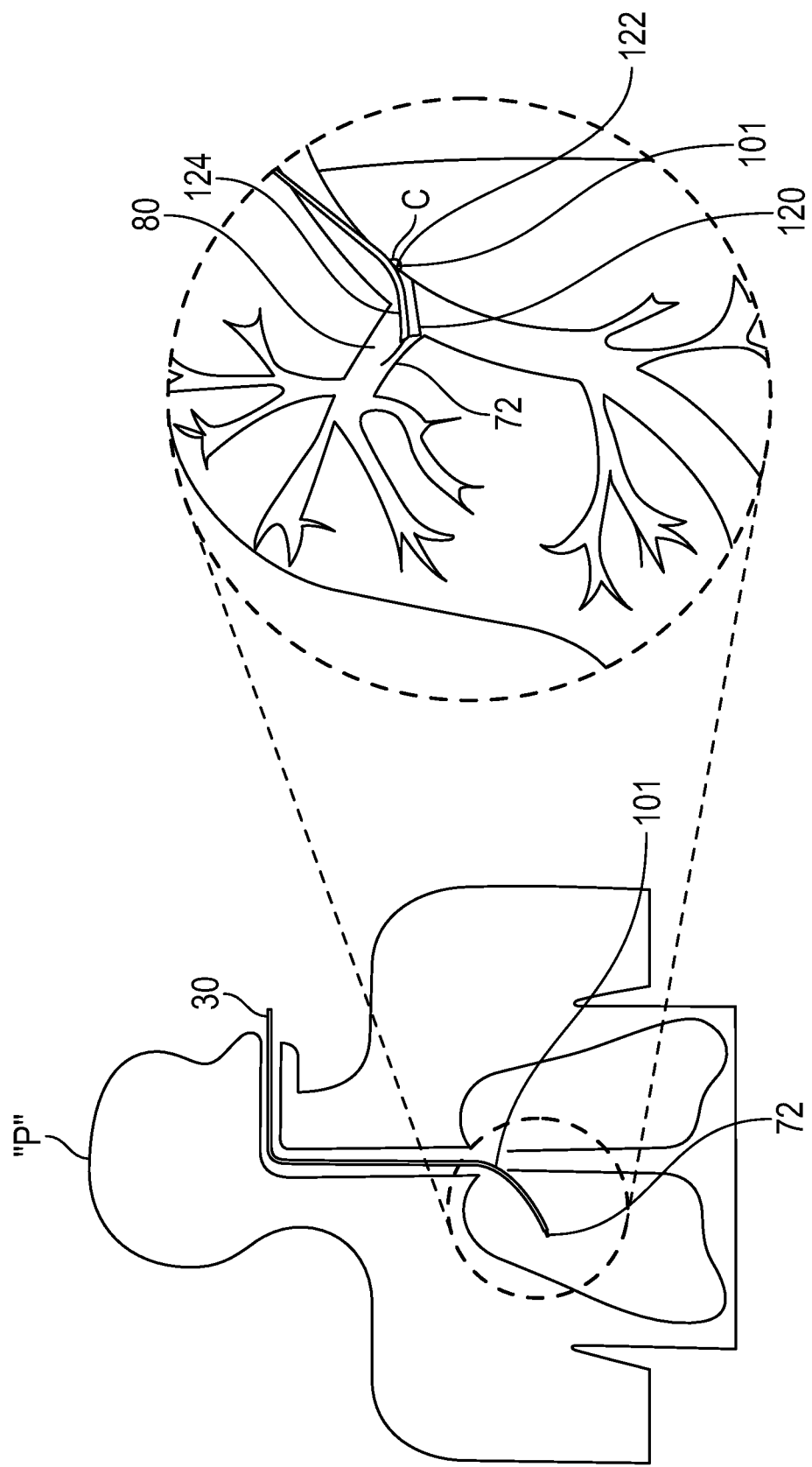

COMPOUND CURVE NAVIGATION CATHETER

CROSS-REFERENCE TO RELATED APPLICATIONS

This application is a continuation of U.S. patent application Ser. No. 15/069,214, filed Mar. 14, 2016, entitled COMPOUND CURVE NAVIGATION CATHETER.

INTRODUCTION

The present disclosure relates to a navigation catheter. More particularly, the present disclosure relates to a navigation catheter having a compound curve at a distal portion. Additionally, the present disclosure relates to a method of manufacturing a navigation catheter.

BACKGROUND

Microwave ablation systems may be utilized for treating various maladies, e.g., cancerous growths on different organs, such as, for example, the liver, brain, heart, lung, and kidney. A microwave ablation system may include a microwave energy source, an ablation probe, and one or more guide members, e.g., a navigation catheter, that are used to guide a microwave ablation probe adjacent target tissue. The navigation catheter, as well as the microwave ablation probe, is typically relatively thin and flexible to allow a clinician to navigate the navigation catheter through a luminal network of an organ, e.g., a lung. In certain instances, a sensor may be positioned within the navigation catheter to facilitate positioning a distal end of the navigation catheter adjacent target tissue. A location of the distal end of the navigation catheter is then recorded.

Once the location of the navigation catheter is obtained, the sensor may be removed from the navigation catheter and one or more surgical instruments (e.g., biopsy, forceps, cytology brush, aspirating needles, ablation catheters, etc.) may be inserted through the navigation catheter and positioned at or extended from the navigation catheter. Extending the surgical instrument from or even advancing the surgical instrument to the distal end of the navigation catheter may cause the distal end of the navigation catheter to deflect from its original position and move relative to the target tissue.

Currently, existing navigation catheters include a curved distal end, and while these catheters are suitable for their intended purposes, deflection of the curved distal end of the navigation catheter (e.g., as a result of the surgical instrument being extended from or positioned at the distal end) after the location has been determined, can make it difficult for a clinician to accurately position tools and maintain tissue target trajectory. As can be appreciated, this, in turn, may decrease target tissue sampling and treatment efficacy.

SUMMARY

One aspect of the present disclosure is directed to a catheter assembly for navigation within a luminal structure. The catheter assembly includes a flexible catheter and a control handle. The flexible catheter includes a proximal portion adjacent a proximal end and a distal portion adjacent a distal end and defining a longitudinal axis. Additionally, the flexible catheter defines a lumen extending therethrough and is configured to enable translation of an instrument from the proximal end to the distal end. The distal portion of the flexible catheter forms a compound curve. The compound curve includes an elbow bend and a radially curved portion. The elbow bend deflects the distal portion of the flexible catheter from the longitudinal axis and the radially curved portion extends from the elbow bend deflecting the distal portion about a center point, wherein the elbow bend projects the radially curved portion laterally away from the longitudinal axis. The distal portion comprises a length that ranges from about 5 percent to about 15 percent of an overall length of the flexible catheter. The elbow bend is fully developed within approximately the first 5 to approximately the first 25 percent of the distal portion, and the radially curve portion is fully developed within approximately the first 75 to approximately the first 95 percent of the distal portion. The control handle is disposed at the proximal end of the flexible catheter and is operably coupled to the flexible catheter, thereby enabling the flexible catheter to advance and rotate within a luminal structure. In some embodiments, the flexible catheter is configured for positioning within a bronchoscope.

In one aspect, a sensor is positioned within the lumen of the flexible catheter such that the location of the distal end of the flexible catheter can be located within a luminal structure. The sensor may be attached to a locatable guide adapted to be inserted through the lumen of the flexible catheter.

In one embodiment, the elbow bend deflects the distal portion of the flexible catheter from the longitudinal axis from about 15 degrees to about 90 degrees. In another embodiment, the elbow bend deflects the distal portion of the flexible catheter from the longitudinal axis from about 30 degrees to about 60 degrees. In a further embodiment, the elbow bend deflects the distal portion of the flexible catheter from the longitudinal axis about 45 degrees.

The flexible catheter may contain a range of differing durometer rating. In some embodiments, the proximal portion of the flexible catheter comprises a first durometer rating and the distal portion of the flexible catheter comprises a second durometer rating, wherein the first durometer rating is greater than the second rating of the distal portion.

In one embodiment, the first durometer rating ranges from about 30D to about 80D and the second durometer rating ranges from about 30D to about 63D.

The present disclosure also discloses a method of manufacturing a flexible catheter including a proximal portion adjacent a proximal end, a distal portion adjacent a distal end, an axially extending lumen that is configured to enable translation of an instrument from the proximal end to the distal end, the distal portion including a radially curved portion that curves about a center point, and a control handle at the proximal end of the flexible catheter that is configured to advance and rotate the flexible catheter within a luminal structure.

In aspects, the method includes forming the radially curved portion within a mold, wherein the radially curved portion is fully developed within the range from about 2 to about 3 centimeters. The mold forms the radially curve portion with a curvature ranging from about 45 to about 195 degrees. In another aspect of the method, the mold forms the radially curved portion with a curvature about 180 degrees.

Further, to the extent consistent, any of the aspects described herein may be used in conjunction with any or all of the other aspects described herein.

BRIEF DESCRIPTION OF THE DRAWINGS

Various aspects of the present disclosure are described herein below with reference to the drawings, which are incorporated in and constitute a part of this specification, wherein:

FIG. 8A is a schematic, plan view of a bronchoscope positioned within the lungs of a patient with a compound curve navigation catheter extending distally from the bronchoscope;

FIG. 8B is an enlarged view of the indicated area of detail of FIG. 8A, which shows bifurcations in the luminal network of a patient's airways and the compound curve navigation catheter located therein;

DETAILED DESCRIPTION

Figure 1:
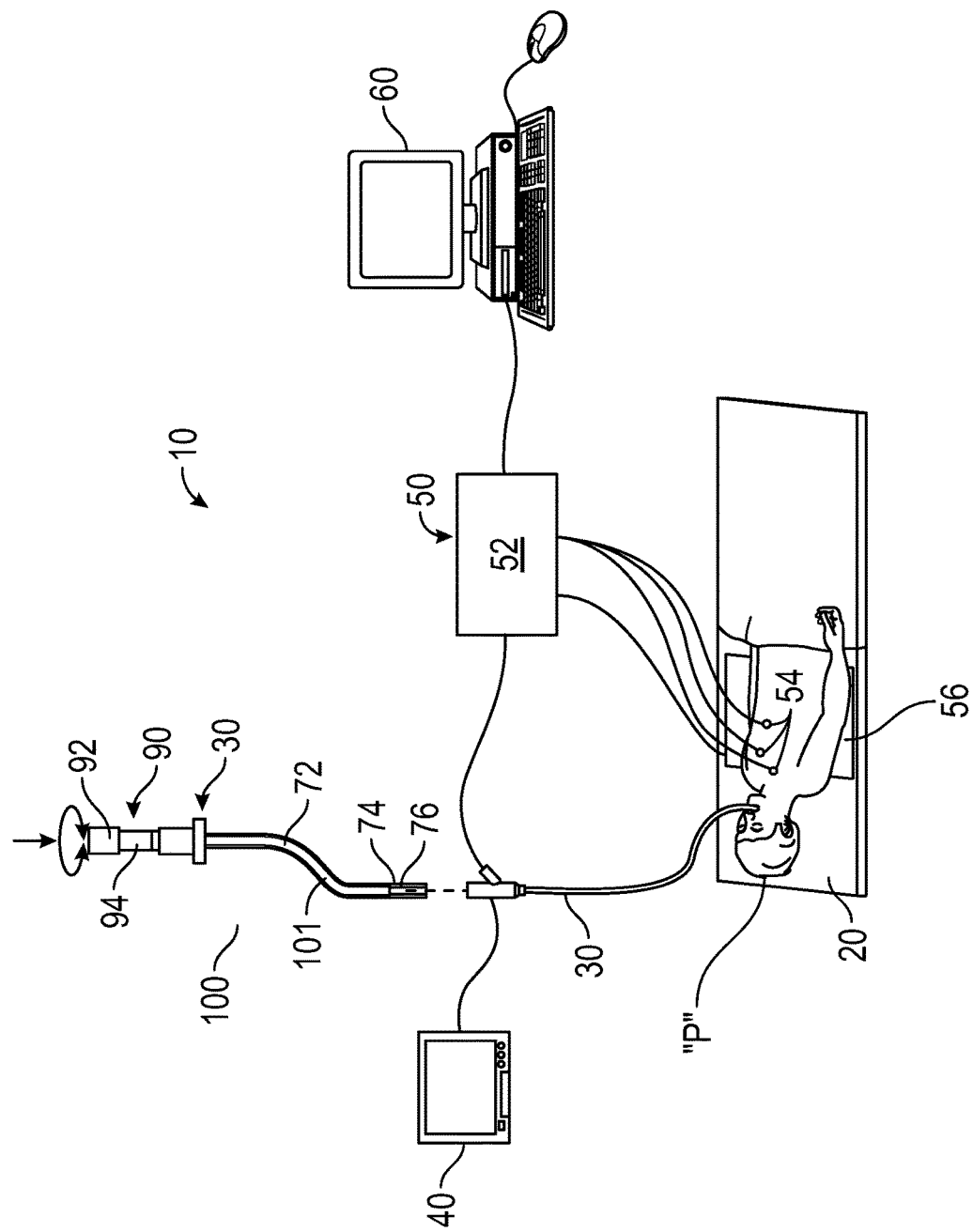
FIG. 1 depicts a compound curve navigation catheter incorporated as part of an electromagnetic navigation system in accordance with the present disclosure.

Generally, the present disclosure is directed in part to a compound curve navigation catheter including a flexible catheter defining a longitudinal axis to facilitate guiding an instrument inserted in the catheter to an otherwise difficult to reach target site within a luminal network of a patient's lungs. Additionally, the present disclosure relates to a method of manufacturing the flexible catheter with a radially curved portion.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Aspects of the present disclosure are described in detail with reference to the figures wherein like reference numerals identify similar or identical elements. As used here, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 2A:
FIGS. 2A-2D are partial perspective views of the distal end portions of a plurality of different surgical instruments in accordance with the present disclosure.
Figure 2B:
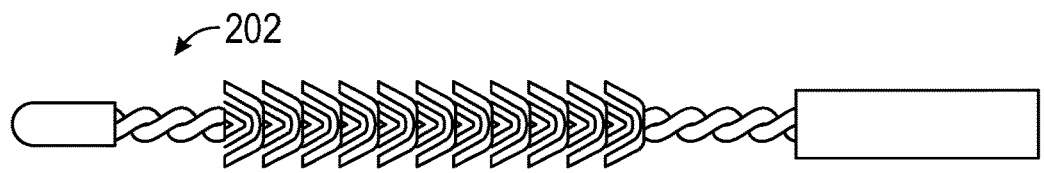
Figure 2C:
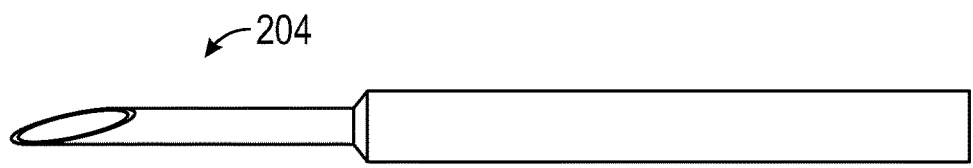
Figure 2D:
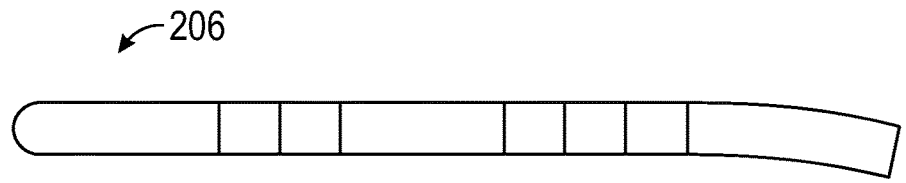

FIG. 1 depicts an electromagnetic navigation (EMN) system 10 in accordance with the present disclosure. The EMN system 10 is configured for planning a pathway to target tissue 80 (FIG. 8B) (planning phase) and navigating a flexible catheter 101 to the target tissue 80 (navigation phase). Following navigation, surgical instruments such as those depicted in FIGS. 2A-2D, including for example, a biopsy forceps 200 (FIG. 2A), a cytology brush 202 (FIG. 2B), an aspirating needle 204 (FIG. 2C), and an ablation catheter 206 (FIG. 2D) may be inserted into the flexible catheter 101 to obtain a tissue sample from the target tissue 80 or to treat target tissue 80 as appropriate. The EMN system 10 generally includes an operating table 20 configured to support a patient "P"; a bronchoscope 30 configured for insertion through the patient "P's" mouth and into the patient "P's" airways; a monitoring equipment 40 coupled to the bronchoscope 30 for displaying video images received from the bronchoscope 30; a tracking system 50 including a tracking module 52, a plurality of reference sensors 54, and a transmitter mat 56; a computer 60 including software and/or hardware used to facilitate pathway planning, identification of the target tissue 80, and navigation to the target tissue 80; a catheter assembly for navigation 100 including flexible catheter 101, a locatable guide 72 insertable into flexible catheter 101 and having a sensor 76 at a distal end 74; and a steering assembly, such as, for example, a control handle 90. For a more detailed description of an exemplary planning phase, reference may be made to U.S. Patent Application Publication No. 2014-0270441 to Matt W. Baker entitled "Pathway Planning System and Method," filed on Mar. 15, 2013, the entire content of which is incorporated by reference herein. Also, for a detailed description of an exemplary navigation phase, reference may be made to U.S. Patent Application Publication No. 2016-0000302 to Andrew E. Brown et al. entitled "System and Method for Navigating within the Lung," filed Jun. 29, 2015, the entire content of which is incorporated herein by reference.

Figure 3:
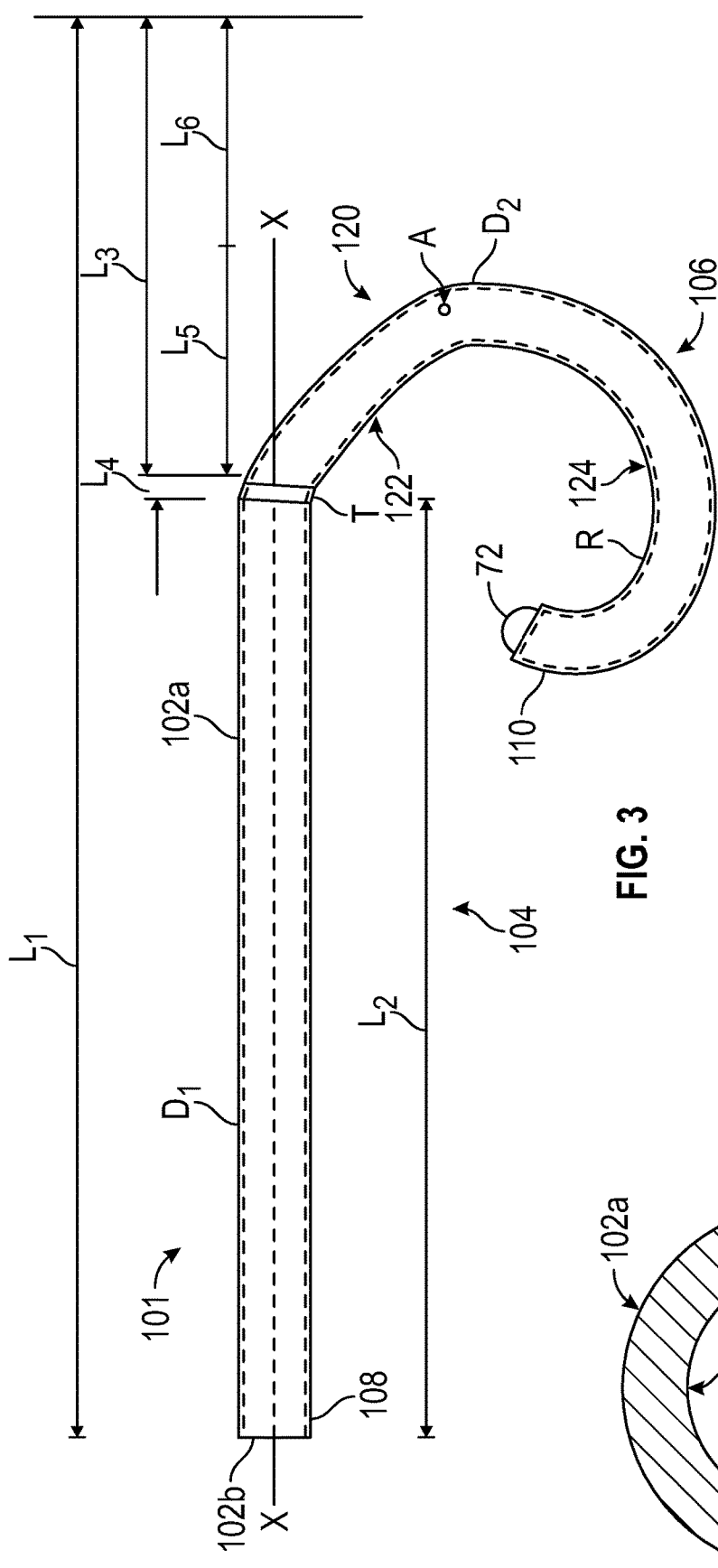
FIG. 3 is a side view of the compound curve navigation catheter shown in FIG. 1.
Figure 3A:
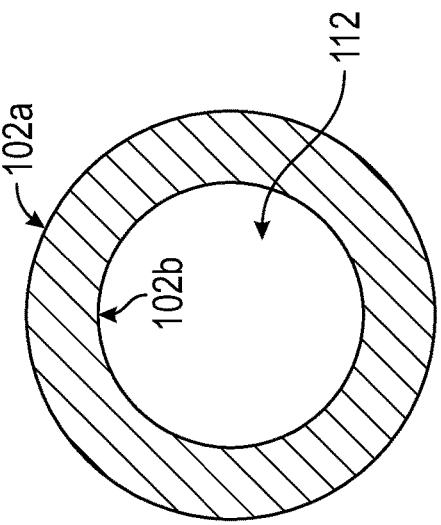
FIG. 3A is a cross-sectional view of the compound curve navigation catheter shown in FIG. 3.

Referring to FIG. 3, the flexible catheter 101 includes a proximal portion 104 adjacent a proximal end 108 and a distal portion 106 adjacent a distal end 110. A longitudinal axis X is defined by a proximal portion 104 of the flexible catheter 101. Proximal portion 104 is substantially straight. The distal portion 106 of the flexible catheter 101 includes a compound curve 120 described in detail below. Flexible catheter 101 further includes an outer surface 102a (FIG. 3A) and an inner surface 102b (FIG. 3A) defining a lumen 112 (FIG. 3A) therein. In one embodiment, the surfaces 102a and 102b may include various properties, including, but not limited to, a low coefficient of friction and lubrication. As shown in FIG. 3, lumen 112 is sized to receive locatable guide 72 or surgical instruments 200-206 (FIGS. 2A-2D).

As shown in FIG. 3, the flexible catheter 101 defines a total length "L1." In one embodiment, the flexible catheter 101 may be formed from materials having a uniform durometer rating along the length "L1." In some embodiments, the proximal portion 104 may be formed from materials having a durometer rating "D1" ranging from about 30D to about 80D, in other embodiments from about 40D to about 70D, in yet other embodiments from about 50D to about 60D along a length "L2" of the flexible catheter 101. However, durometer rating "D1" of proximal portion 104 is not limited to the ranges specified above, and may be greater or less than these specified ranges for a desired application.

In some embodiments, the distal portion 106 may be formed from materials having a durometer rating "D2" ranging from about 20D to about 75D, in other embodiments from about 25D to about 60D, in yet other embodiments from about 30D to about 63D along a length "L3." However, it is also contemplated that durometer rating "D2" of distal portion 106 may be greater or less than these specified ranges. In embodiments, the length "L3" ranges from about 5 percent to about 15 percent, in other embodiments about 2 percent to about 10 percent of the overall length "L1." However, it is also contemplated that length "L3" may be greater or less than these specified ranges. A detailed description of a flexible catheter 101 with varying durometer ratings is found, for example, in U.S. Patent Application Publication No. 2015-0126852 to David M. Costello et al. entitled "Positioning Catheter," filed Jul. 30, 2014, the entire content of which is incorporated herein by reference.

In the EMN system 10 of FIG. 1, during insertion and navigation of flexible catheter 101 and locatable guide 72 to a desired target, the location of the flexible catheter 101 is determined with the help of locatable guide 72, and more particularly, a sensor 76 affixed to distal end 74 of locatable guide 72. In other embodiments, the sensor 76 may be affixed to any of the surgical instruments 200-206. Also, in yet other embodiments, the sensor 76 may be affixed to the flexible catheter 101. In one embodiment, in order to place any of surgical instruments 200-206 into lumen 112 of flexible catheter 101, locatable guide 72 including sensor 76 may need to be removed. The clinician will typically use fluoroscopy to visualize any motion of flexible catheter 101; however, it is very useful to the clinician for positioning purposes to be able to anticipate movement of the flexible catheter 101 upon removal/placement of the surgical instruments 200-206 within lumen 112.

Accordingly, by employing flexible catheter 101 having specific properties (e.g., distal portion including a compound curve and specific durometer ratings), the effect of withdrawing locatable guide 72 and the subsequent insertion of surgical instruments 200-206 can be ascertained with a greater degree of accuracy. In particular, before removing locatable guide 72, the clinician is able to properly place the flexible catheter 101 within the luminal network of the lungs of patient "P" to accommodate for the expected effect of inserting surgical instruments 200-206. Moreover, because each surgical instrument 200-206 has a different effect on the shape of flexible catheter 101 when inserted within lumen 112, each of these may be separately ascertained and understood by the clinician.

In embodiments where the durometer rating of the flexible catheter 101 changes between the proximal portion 104 and the distal portion 106, the flexible catheter 101 includes a transition portion "T", as shown in FIG. 3. The transition portion "T" may be formed from suitable connection methods, including, but not limited to, over molding, thermal fusion, and ultrasonic welding. The distance between the proximal end 108 and the transition portion "T" is length "L2." In some embodiments, the length "L2" ranges from about 90 centimeters to about 100 centimeters, in other embodiments from about 93 centimeters to about 98 centimeters. The distance between distal end 110 and transition portion "T" is length "L3". In some embodiments, the length "L3" ranges from about 8 centimeters to about 11 centimeters, in other embodiments from about 9 centimeters to about 10 centimeters. As shown in FIG. 3, the length of transition portion "T" is a length "L4." In one embodiment, length "L4" is approximately 1 centimeter.

With continued reference to FIG. 3, the distal portion 106 includes a compound curve 120. In some embodiments, the compound curve 120 includes an elbow bend 122 and a radially curved portion 124. The compound curve 120 is located entirely within the length "L3" of the flexible catheter 101. As seen in FIG. 3, the elbow bend 122 extends the length "L5" of the distal portion 106. In some embodiments, the length "L5" ranges from about 1 percent to about 25 percent, in other embodiments from about 3 percent to about 22 percent, in yet other embodiments from about 5 percent to about 20 percent of the overall length of "L3." However, it is contemplated that length "L5" of distal portion 106 may be greater or less than these specified ranges. The length "L5" is initiated at a distal side of the transition portion "T" and terminates at a proximal side of the radially curved portion 124. Also seen in FIG. 3, the radially curved portion 124 extends the length "L6" of the distal portion 106. In some embodiments, the length "L6" ranges from about 75 percent to about 99 percent, in other embodiments from about 78 percent to about 97 percent, in yet other embodiments from about 80 percent to about 95 percent of the overall length of "L3." However, it is also contemplated that length "L6" of distal portion 106 may be greater or less than these specified ranges. The length "L6" is initiated at a distal side of the length "L5" of the distal portion 106 and terminates at the distal end 110 of the flexible catheter 101. The point of transition between the elbow bend 122 and the radially curved portion 124 is indicated in FIG. 3 as point A.

Figure 4A:
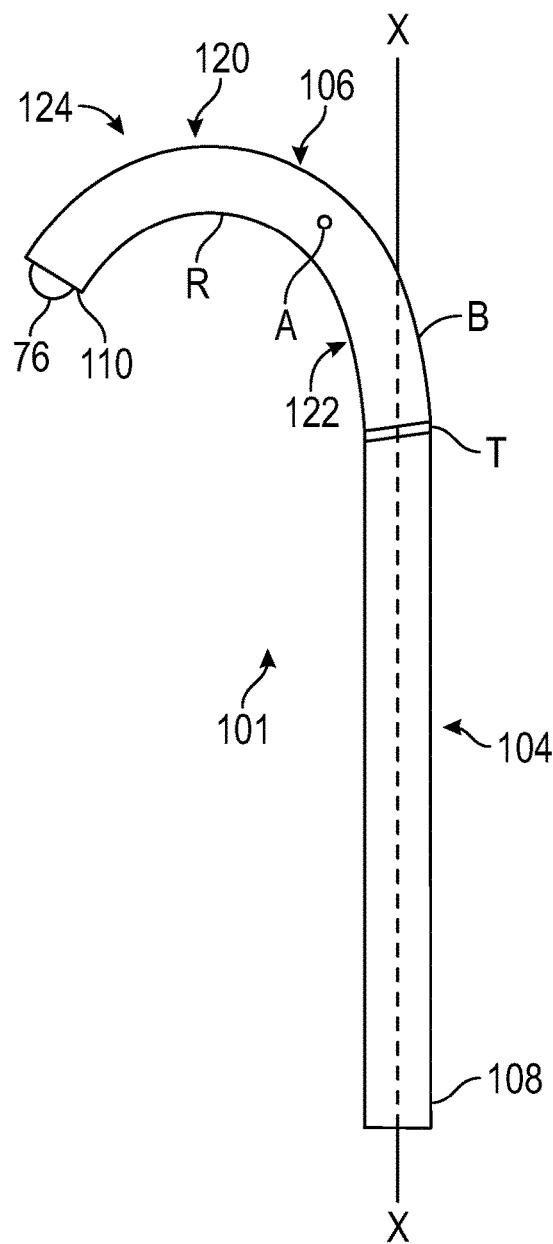
FIGS. 4A-4B and 5A-5B are side partial views showing the compound curve navigation catheter having an elbow bend and a radially curved portion.
Figure 4B:
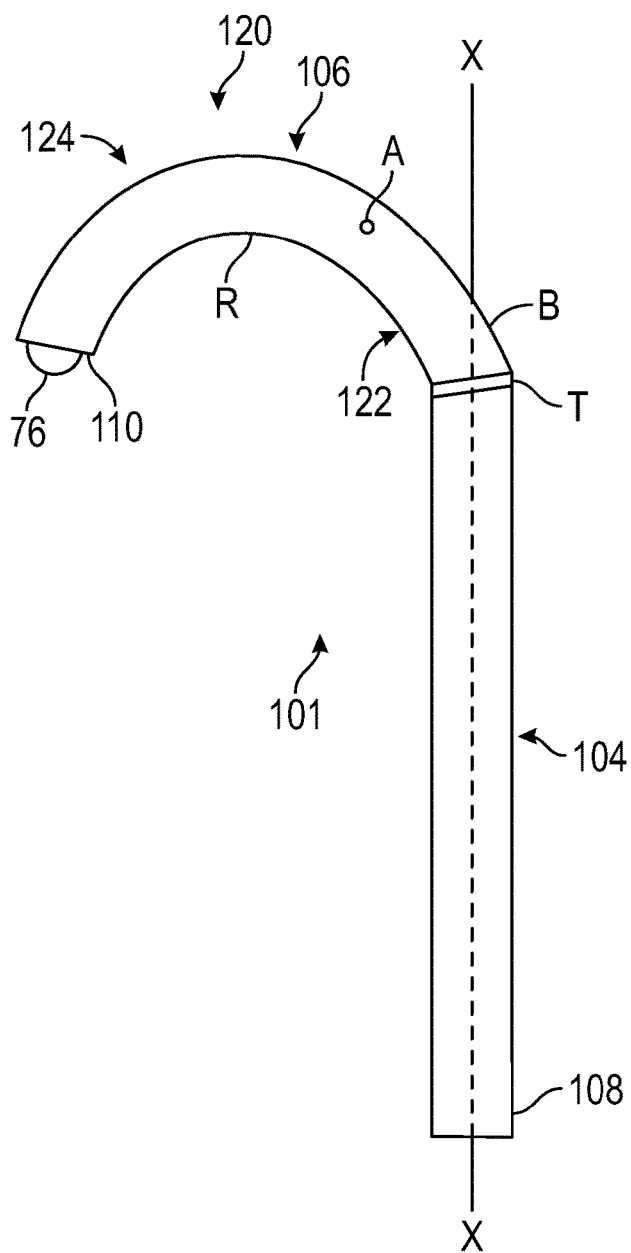
Figure 5A:
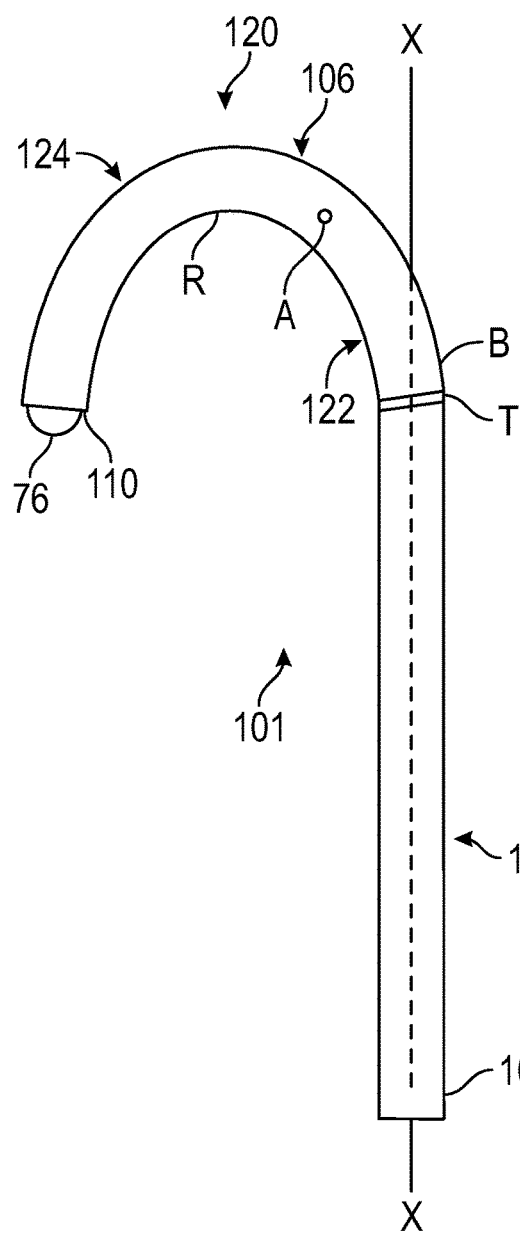
Figure 5B:
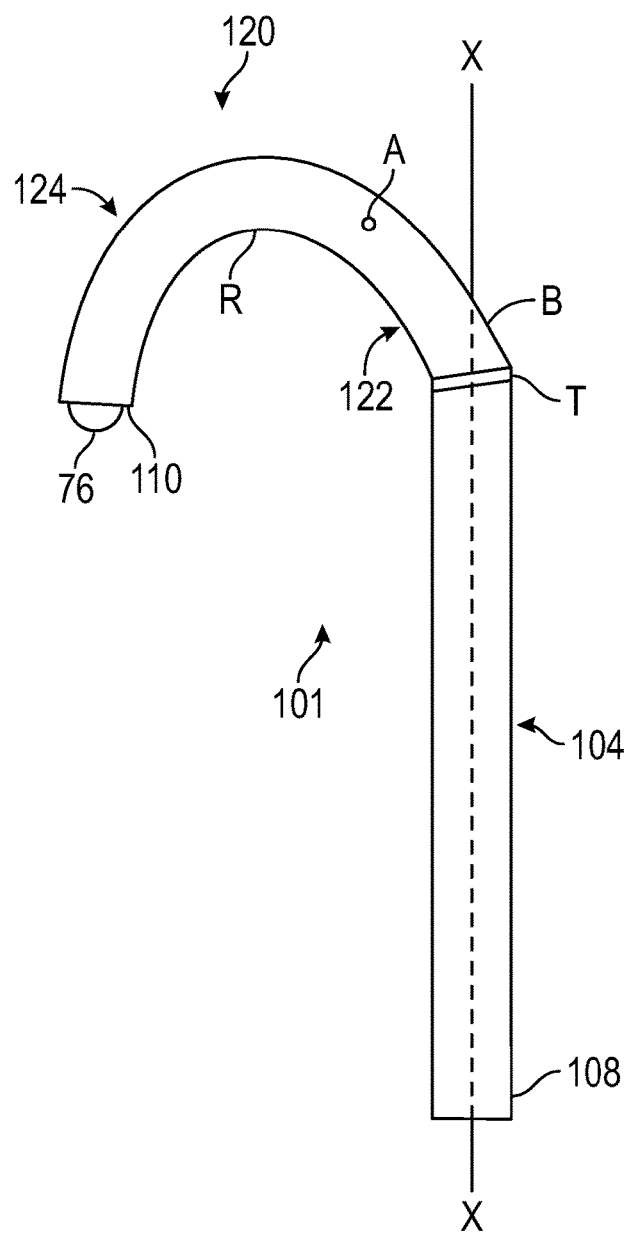

Now looking at FIGS. 4A-4B and 5A-5B, different embodiments of the compound curve 120 are illustrated. The elbow bend 122 and radially curved portion 124 of the compound curve 120 are defined with reference to the longitudinal axis X. The elbow bend 122 deflects the distal portion 106 away from the longitudinal axis X. In some embodiments, elbow bend 122 may include a bend that ranges between about 15 degrees to about 90 degrees, in other embodiments about 30 degrees to about 60 degrees, in yet other embodiments about 40 degrees to about 55 degrees away from the longitudinal axis X. However, it is contemplated that the degree of bend can be greater or lesser than these specified ranges. In some embodiments, the elbow bend 122 includes a bend "B" of 15 degrees (FIGS. 4A and 5A). In other embodiments, the elbow bend 122 includes a bend "B" of about 45 degrees (FIGS. 4B and 5B).

Figure 6A:
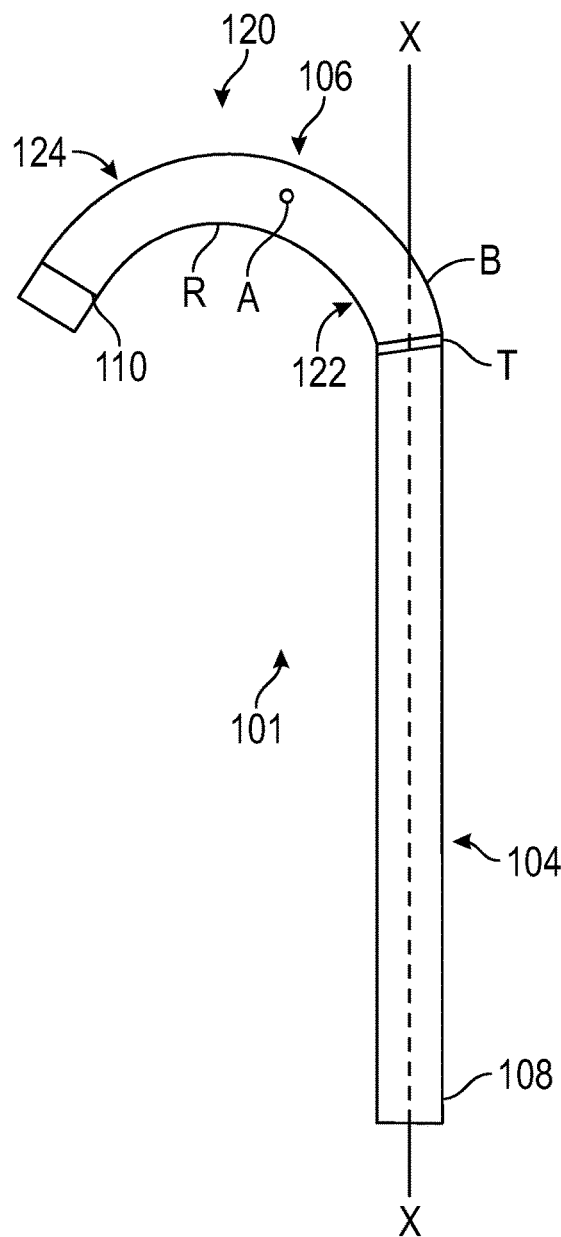
FIGS. 6A and 7A are side partial views showing the compound curve navigation catheter having an elbow bend and a radially curved portion without an instrument disposed therein.
Figure 6B:
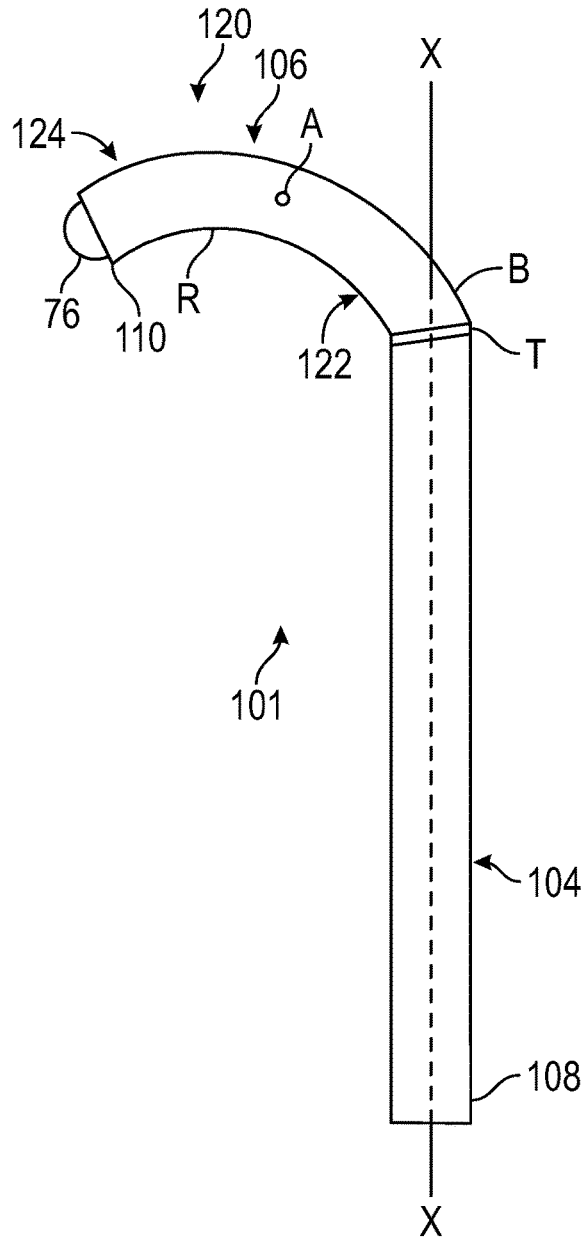
FIGS. 6B and 7B are side partial views showing the compound curve navigation catheter having an elbow bend and a radially curved portion with an instrument disposed therein.
Figure 7A:
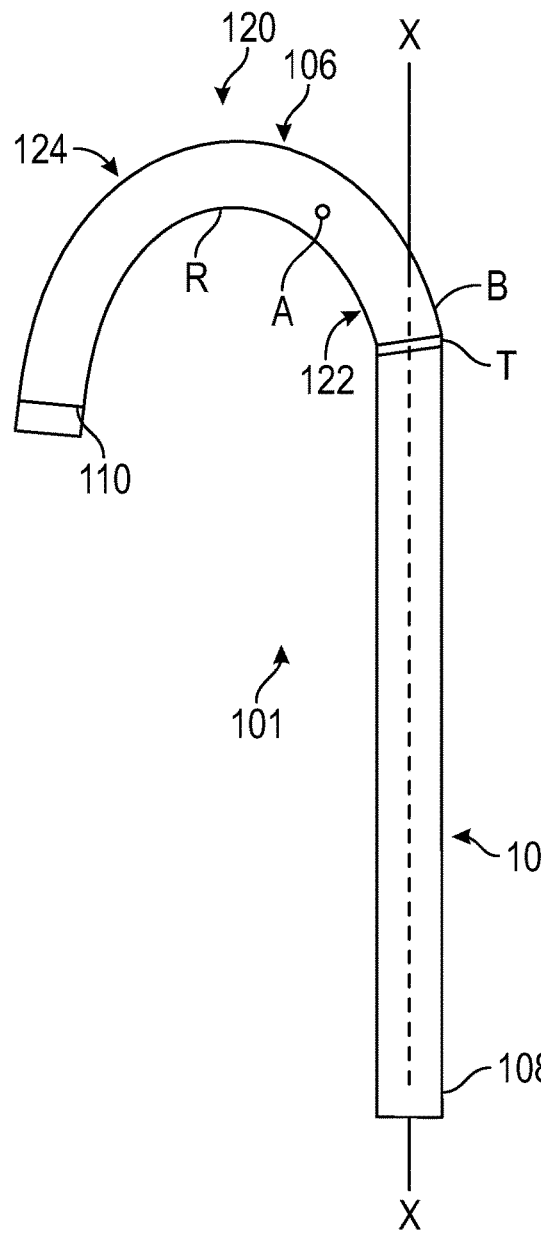
Figure 7B:
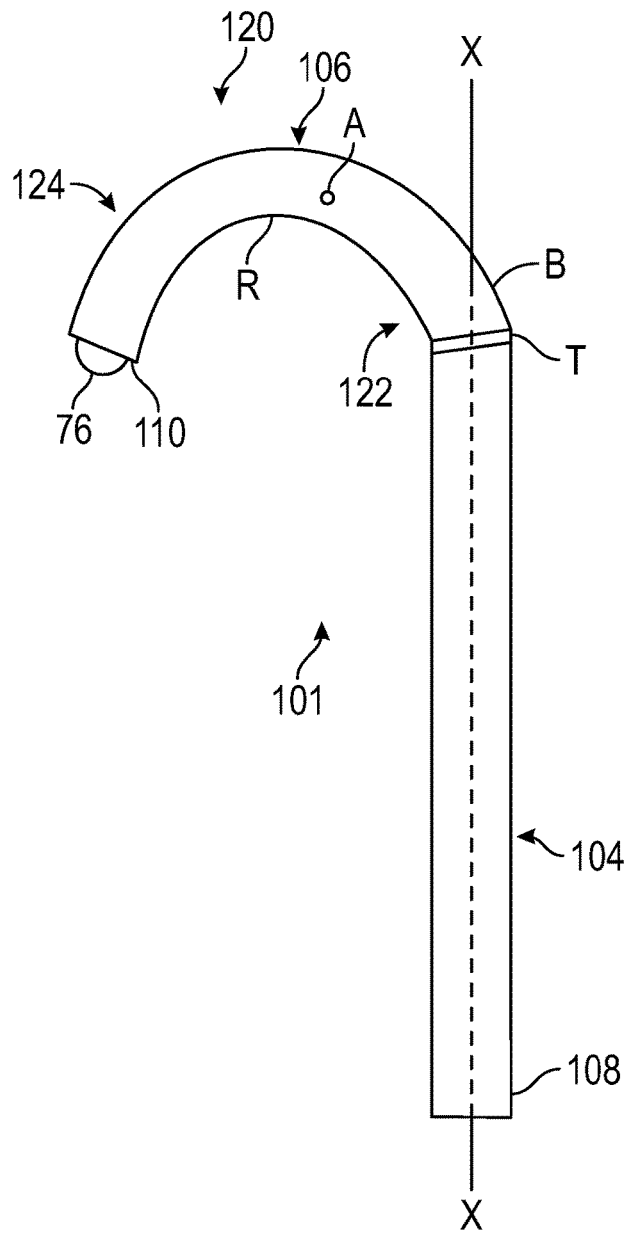

With continued reference to FIGS. 4A-4B and 5A-5B, the radially curved portion 124 extends from the elbow bend 122, wherein the elbow bend 122 laterally projects the radially curved portion 124 away from the longitudinal axis X of the flexible catheter 101. Radially curved portion 124 is defined by a radius of curvature "R." Radially curved portion 124 may have varying lengths such that it circumscribes 45, 90, and 180 degrees (see e.g., FIGS. 4A-4B and FIGS. 5A-5B); however, others may be employed without departing from the scope of the present disclosure. The radially curved portion 124 may be fully developed in a range of about 1 centimeter to about 7 centimeters, in another embodiment from about 2 centimeters to about 6 centimeters, and in yet another embodiment from 2.5 centimeters to about 5.5 centimeters; however, other ranges may be employed without departing from the scope of the present disclosure. In other embodiments, the radially curved portion 124 may be fully develop in 2.5 centimeters, 3 centimeters or 3.5 centimeters. FIGS. 6A-6B and FIGS. 7A-7B depict side views of additional embodiments of the flexible catheter 101. In one embodiment, compound curve 120 includes an elbow bend 122 with a bend "B" of about 45 degrees and a radially curved portion 124 circumscribing about 90 degrees (FIGS. 6A-6B). In accordance with the instant disclosure, when locatable guide 72 (FIG. 6B) is disposed in the flexible catheter 101 such that sensor 76 is extended past distal end 110, the deflection of the compound curve 120 is limited (compare FIG. 6A with 6B). Similar results are attained when the compound curve 120 includes an elbow bend 122 with a bend "B" of about 45 degrees and a radially curved portion 124 circumscribing about 180 (FIG. 7A-7B) or an elbow bend 122 with a bend "B" of about 15 degrees and a radially curved portion 124 circumscribing about 90 degrees or an elbow bend 122 with a bend "B" of about 15 degrees and a radially curved portion 124 circumscribing about 180 degrees (not shown).

Now referring to FIG. 8A and FIG. 8B, the elbow bend 122 may allow a more precise trajectory of the projected deflection of the radially curved portion 124. Further, elbow bend 122 may act as an anchor for the radially curved portion 124 of the flexible catheter 101 once placed in a luminal network at the desired location. In embodiments where the elbow bend 122 acts as an anchor, the clinician can use the anchoring point of the elbow bend 122 as an origin point for predicting the amount of deflection of the radially curved portion 124 once a surgical instrument, such as one of surgical instruments 200-206, is introduced into the lumen 112 of the flexible catheter 101. The location where the elbow bend 122 acts as an anchor is indicated by point C (FIG. 8B) where the proximal portion of the elbow bend 122 (e.g., proximate the transition T) contacts the airway wall.

In some embodiments, the elbow bend 122 may allow the radially curved portion 124 to reach farther within the luminal network. As indicated above, by the elbow bend 122 acting as an anchor for the radially curved portion 124, the radially curved portion 124 may allow an inserted surgical instrument, such as one of surgical instruments 200-206, to reach a targeted tissue area farther and/or higher within the luminal network. This is accomplished because the elbow bend 122 provides an angled structure to the flexible catheter 101 allowing a clinician to completely utilize the radially curve portion 124. Also, the elbow bend 122 enables the radially curved portion 124 to be more pronounced, which enhances the ability of the radially curved portion 124 to reach farther within the luminal network.

The clinician may select the appropriate combination of bend "B" and the angle of the radially curved portion 124 to be used to navigate to differing areas of the patient "P's" airways. For example, in one embodiment, the compound curve 120 including an elbow bend 122 with a bend "B" of about 45 degrees and a radially curved portion 124 circumscribing 180 degrees may be used for directing locatable guide 72 and sensor 76 to a posterior portion of the upper lobe of the patient "P's" airways.

Figure 10:
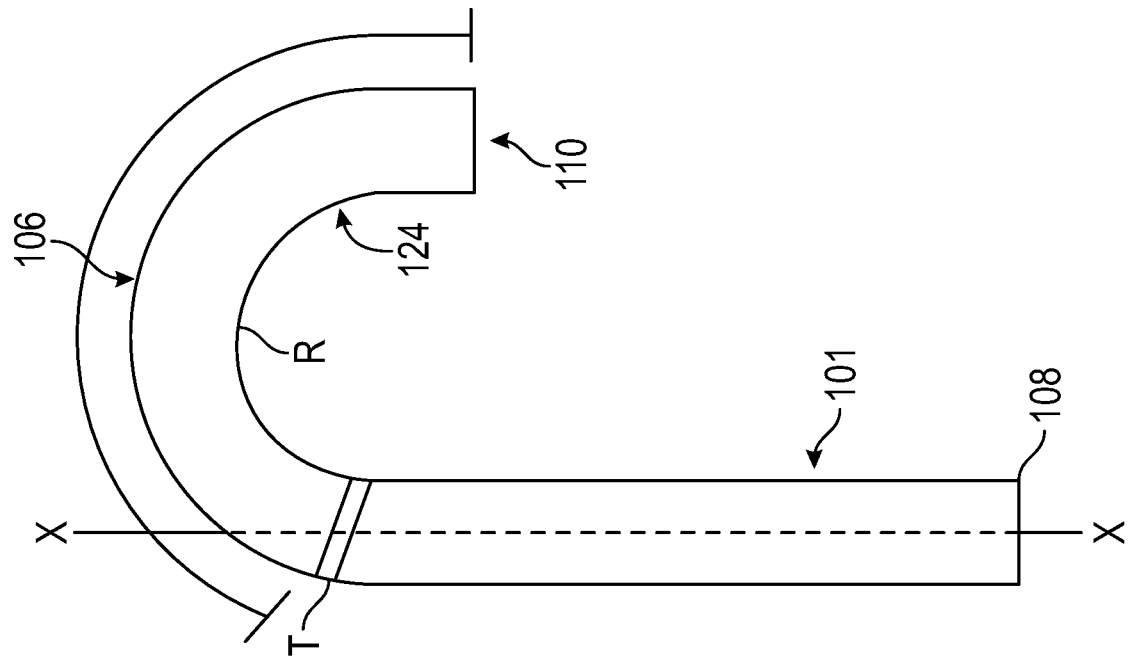
FIG. 10 is a side partial view showing the distal portion of the compound curve navigation catheter having a radially curved portion.
Figure 9:
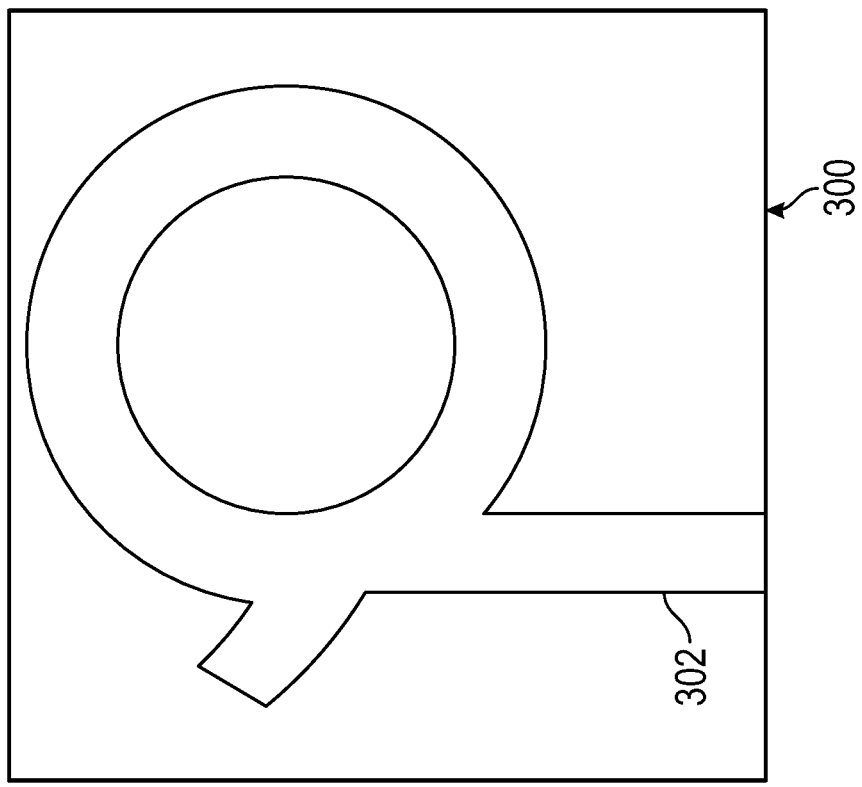
FIG. 9 is a top view of a mold for forming the distal portion of a flexible catheter according to the present disclosure.

Referring now to FIGS. 9 and 10, another embodiment of the flexible catheter 101 and a method of manufacturing the flexible catheter 101 will be described. The distal portion 106 of the flexible catheter 101 may solely contain a radially curved portion 124. As described above, radially curved portion 124 may include a radius of curvature "R" and circumscribe 45, 90, or 180 degrees; however, other radii of curvature "R" and other magnitudes of angles circumscribed may be employed without departing from the scope of the present disclosure. In some embodiments, the radially curved portion 124 may be fully developed in a range from about 2 centimeters to about 3 centimeters, and in other embodiments from about 2.25 centimeters to about 2.75 centimeters; however, other ranges may be employed without departing from the scope of the present disclosure.

With continued reference to FIGS. 9 and 10, the flexible catheter 101 is manufactured using a mandrel (not shown). The inner surface 102b of the flexible catheter 101 is slid over a mandrel, such that the mandrel passes through the lumen 112. The mandrel provides rigidity to the flexible components of the flexible catheter 101 while the flexible catheter 101 is being assembled. The lumen 112 has an inner diameter (not shown) defined by the inner surface 102b. The inner diameter of the flexible catheter 101 is substantially equal to but slightly larger than an outer diameter of the mandrel and has a length substantially equal to a length of the mandrel. The mandrel may be coated with a PTFE coating to assist in sliding the inner surface 102b of the flexible catheter 101 over the mandrel and to prevent the inner surface 102b of the flexible catheter 101 from bonding to the mandrel. The outer diameter of the mandrel is substantially equal to a desired inner diameter of the lumen of the flexible catheter 101 and the length of the mandrel is longer than a final desired length of the flexible catheter 101. The mandrel may have a diameter ranging from about 0.127 centimeters to about 0.254 centimeters, in other embodiments from about 0.154 centimeters to about 0.230 centimeters. Also, the mandrel may have a length ranging from about 76 centimeters to about 230 centimeters, in other embodiments from about 90 centimeters to about 200 centimeters, in yet other embodiments from about 120 centimeters to about 160 centimeters. After the formation of the flexible catheter 101 over the mandrel, the flexible catheter 101 is placed within a mold 300 to form the radially curved portion 124. Distal portion 106 of the flexible catheter 101 is placed within a hollowed out section 302 of mold 300. The hollowed out section 302 resembles a "p" shape. The upper curve of the hollowed out section 302 is shaped to fully develop the radially curved portion 124 within the desired range of curvature. As described above, radially curved portion 124 may be fully developed within 2 to 3 centimeters; however, other ranges may be employed without departing from the scope of the present disclosure. Also, the hollowed out section 302 may be shaped in other forms without departing from the scope of the present disclosure. In some embodiments, mold 300 may include a first half and a second half (not shown). Each half may include a hollowed out section, similar to hollowed out section 302. Additionally, the first half has a similar orientation to the second half so that the hollowed out sections in each half align with one another when the first half engages with the second half After distal portion 106 of the flexible catheter 101 is placed within the hollowed out section 302, sufficient heat and/or pressure are applied to the distal portion 106 of flexible catheter 101 in order for radially curved portion 124 to be formed.

In another embodiment, the compound curve 120 of the flexible catheter 101 may be formed by mold 300. Distal portion 106 of the flexible catheter 101 is placed within the hollowed out section 302 of mold 300. Hollowed out section 302 may include a shape that would allow the formation of the elbow bend 122 with a bend "B" and the radially curved portion 124 with a radius of curvature "R".

The flexible catheter 101 may be formed from any suitable material, including but not limited to, rubbers and plastics acceptable for surgical and medical use. It is contemplated that a suitable material (not specifically shown) may include a braided support structure formed from metals or alternatively one or more non-conductive fibrous materials such as aramid fibers, sold under the brand-named KEVLAR® available from Dupont or other aramid fibers to provide additional resilience and to maintain lumen 112 in a generally open configuration to ease the passage of locatable guide 72, surgical instruments 200-206, and other tools therethrough. A detailed description of the construction of a flexible catheter and a method of manufacturing are found, for example, in U.S. Provisional Patent Application No. 62/222,449 to David M. Costello et al. entitled "Method of Manufacturing and Elongated Catheter Having Sensor and an Extended Working Channel," filed Sep. 23, 2015, the entire content of which is incorporated herein by reference.

Referring back to FIG. 1, a catheter assembly for navigation 100 includes control handle 90, a grip 92, and a telescopic shaft 94, which are operably connected to flexible catheter 101. By rotating grip 92 and translating the telescopic shaft 94, the clinician is able to steer the flexible catheter 101 to the target tissue 80 (FIG. 8B) using one hand. These movements of control handle 90 enable the clinician to navigate the flexible catheter 101 through the tortuous path of a luminal network such as the patient "P's" airways, and direct advancement of the flexible catheter 101 at each bifurcation. An example of control handle 90 is currently manufactured and sold under the name EDGE™ by Medtronic. Control handle 90 may be ergonomically shaped to facilitate grasping and/or rotation of flexible catheter 101. In one embodiment, a plurality of rib portions (not explicitly shown) are provided along a length of control handle 90 to facilitate grasping and rotation of the flexible catheter 101.

EMN system 10 includes tracking system 50 that is utilized for creating a visual image of patient location registration and luminal navigation during the navigation phase. In embodiments, tracking system 50 is a six degrees-of-freedom electromagnetic tracking system similar to those disclosed in U.S. Application Patent Publication No. 2016-0000302 to Andrew E. Brown et al. entitled "System and Method for Navigating within the Lung," filed Jun. 29, 2015, the entire content of which is incorporated herein by reference. However, it is contemplated that other suitable positioning measuring systems as well as other suitable configurations may also be utilized. As depicted in FIG. 1, tracking system 50 includes tracking module 52, the plurality of reference sensors 54, and transmitter mat 56. Transmitter mat 56 of tracking system 50 is positioned beneath patient "P" and generates an electromagnetic field (not explicitly shown) around at least a portion of patient "P." Tracking system 50 is configured for use with catheter assembly for navigation 100.

Using tracking module 52 and the generated electromagnetic field of transmitter mat 56, the position of the plurality of reference sensors 54 and sensor 76 may be determined as locatable guide 72 and flexible catheter 101 are navigated through the luminal network. More particularly, one or more of the plurality of reference sensors 54 are attached to the chest of the patient "P." The coordinates of the plurality of reference sensors 54 and sensor 76 on the locatable guide 72 within the electromagnetic field generated by transmitter mat 56 are sent to computer 60, which includes the appropriate software to determine their location with reference to a navigation plan.

The locatable guide 72 and the flexible catheter 101 are configured for insertion through a working channel (not explicitly shown) of the bronchoscope 30 into the patient "P's" airways. However, it is contemplated that locatable guide 72 and flexible catheter 101 may alternatively be used without the bronchoscope 30. In embodiments, the locatable guide 72 and the flexible catheter 101 are selectively lockable relative to one another via a locking mechanism (not explicitly shown).

Having described the components of the EMN system 10 generally, the following describes their interaction and implementation in combination with planning and navigation software resident on computer 60. An example of such software for planning and navigation is the iLogic™ planning and navigation suites of software currently sold by Medtronic.

During the planning phase, computed tomographic (CT) images are taken of the patient "P's" lungs. Computer 60 utilizes data generated from the CT to create a three-dimensional mode of patient "P's" airways. With the planning software, the clinician may select a pathway to the target tissue 80. Once a suitable pathway is selected, the pathway is saved and exported to a navigation component of the software for use during the navigation phase(s). Additionally, by selecting a suitable pathway to the target tissue 80, the clinician is able to choose the compound curve 120 with an elbow bend 122 with a bend of "B" and a radially curved portion 124 with a radius of curvature "R" and circumscribing an angle best configured to reach target tissue 80. Following this selection but prior to beginning the procedure, the location of patient "P" on transmitter mat 56 must be registered. During registration, the location of the target tissue 80 generated during the planning phase from the three-dimensional model of the patient "P's" airways is coordinated with the patient "P's" airways as observed through bronchoscope 30 and sensed using the sensor 76 when flexible catheter 101 is inserted into the lungs. As a result, the navigation phase can be undertaken with precise knowledge of the location of sensor 76 particularly in portions of the patient "P's" airways where bronchoscope 30 cannot reach. Further details of such a registration technique and its implementation in luminal navigation can be found in U.S. Patent Application Publication. No. 2016-0000356 to Andrew E. Brown et al. entitled "Real-Time Automatic Registration Feedback," filed Jul. 2, 2015, the entire content of which is incorporated herein by reference. However, in embodiments, other suitable techniques are also contemplated.

As described, sensor 76 is integrated into distal end 74 of locatable guide 72 and is configured to output signals that indicate the position and orientation of locatable guide 72 in six degrees of freedom, relative to a reference coordinate system. In embodiments, as shown in FIG. 1, and FIGS. 8a-8b, locatable guide 72 is inserted into the flexible catheter 101 such that sensor 76 projects from the distal end 110 of the flexible catheter 101. The flexible catheter 101, together with locatable guide 72, is inserted through bronchoscope 30 and into the airways of the patient "P." Initially, bronchoscope 30, including flexible catheter 101 and locatable guide 72, are advanced through patient "P's" mouth and into the luminal network of patient "P". When bronchoscope 30 is wedged and unable to advance any farther through the luminal network of patient "P," the flexible catheter 101 and locatable guide 72 are advanced passed bronchoscope 30. As discussed above, flexible catheter 101 and locatable guide 72 are advanced to target tissue 80 by translating and rotating control handle 90.

In one embodiment, automatic registration of the location of sensor 76 is undertaken by simply moving locatable guide 72 through the airways of the patient "P." More specifically, while locatable guide 72 is moving through the airways of the patient "P," data pertaining to the locations of sensor 76 are recorded using tracking system 50. A shape resulting from these locations and movements data are compared with an interior geometry of airways of patient "P" from the three-dimensional model generated during the planning phase. Based on this comparison, a location correlation between the shape and the three-dimensional model of patient "P's" airways is determined, e.g., utilizing software on computer 60. The software on computer 60 aligns, or registers, an image representing a location of sensor 76, with the three-dimensional model of the airways of the patient "P" or the two-dimensional images generated from the three-dimension model, which are based on the recorded location data and an assumption that locatable guide 72 remains located in non-tissue space (e.g., within the air filled cavities) in the airways of patient "P".

After the planning phase has been completed (e.g., target tissue 80 has been identified and the pathway thereto selected), and the registration has been completed, EMN system 10 may be utilized to navigate locatable guide 72 through patient "P's" airway to target tissue 80. To facilitate such navigation, computer 60, monitoring equipment 40, and/or any other suitable display may be configured to display the three-dimensional model of the patient "P's" airways or two-dimensional model of the patient "P's" airways or two-dimensional images generated from the three-dimensional model of the patient "P's" airways and the two-dimensional images may include the selected pathway from the current location of sensor 76 to target tissue 80.

Once locatable guide 72 has been successfully navigated to target tissue 80, thus completing the navigation phase, locatable guide 72 may be removed from the flexible catheter 101, leaving the flexible catheter 101 in place as a guide channel for guiding surgical instruments, such as, for example, biopsy forceps 200, cytology brush 202, aspirating needle 204, and ablation catheter 206 to target tissue 80. Prior to removal of locatable guide 72 or following insertion of one of surgical instruments 200-206, placement may be confirmed (e.g., within and/or adjacent the target tissue 80) utilizing one or more imaging modalities. For example, CT, ultrasound, fluoroscopy, and other imaging modalities may be utilized individually or in combination with one another.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplification of particular embodiments. Those skilled in the art will envision other modifications within the scope and spirit of the claims appended hereto.

What is claimed is:

1. A catheter assembly for navigation within a patient's airways, comprising:
   a flexible catheter defining a lumen and including a proximal portion and a distal portion, the distal portion having a distal end defining an opening that is in communication with the lumen and configured to allow passage of an instrument out of the flexible catheter;
   a control handle disposed at the proximal portion of the flexible catheter and configured to advance and rotate the flexible catheter within the patient's airways;
   a pre-formed compound curve formed on the distal portion of the flexible catheter and having a first end connected to a distal end of the proximal portion of the flexible catheter, the pre-formed compound curve including:
      an elbow bend deflecting the distal portion of the flexible catheter from a longitudinal axis defined by the proximal portion of the flexible catheter; and
      a radially curved portion extending from the elbow bend to a distal-most end surface of the distal portion of the flexible catheter and deflecting the distal portion about a center point, the elbow bend projecting the radially curved portion laterally away from the longitudinal axis.

2. The catheter assembly according to claim 1, wherein the elbow bend has a radius of curvature that is different than a radius of curvature of the radially curved portion.

3. The catheter assembly according to claim 1, wherein the distal-most end surface of the distal portion of the flexible catheter faces the longitudinal axis defined by the proximal portion of the flexible catheter.

4. The catheter assembly according to claim 1, wherein a majority of the pre-formed compound curve is disposed distally of the distal end of the proximal portion of the flexible catheter.

5. The catheter assembly according to claim 1, wherein the elbow bend deflects the distal portion of the flexible catheter about 15 degrees to about 90 degrees from the longitudinal axis.

6. The catheter assembly according to claim 1, wherein the elbow bend deflects the distal portion of the flexible catheter about 30 degrees to about 60 degrees from the longitudinal axis.

7. The catheter assembly according to claim 1, wherein the proximal portion of the flexible catheter has a first durometer rating and the distal portion of the flexible catheter has a second durometer rating different from the first durometer rating.

8. The catheter assembly according to claim 7, wherein the first durometer rating is greater than the second durometer rating and the first durometer rating ranges from about 30D to about 80D and the second durometer rating ranges from about 30D to about 63D.

9. The catheter assembly according to claim 1, wherein the length of the distal portion of the flexible catheter ranges from about 5 percent to about 15 percent of an overall length of the flexible catheter.

10. A catheter assembly for navigation within a patient's airways, comprising:
    a flexible catheter defining a lumen and including a proximal portion and a distal portion, the distal portion having a distal end defining an opening that is in communication with the lumen and configured to allow passage of an instrument out of the flexible catheter; and
    a pre-formed compound curve formed on the distal portion of the flexible catheter and including:
       an elbow bend deflecting the distal portion of the flexible catheter from a longitudinal axis defined by the proximal portion of the flexible catheter; and
       a radially curved portion extending from the elbow bend to a distal-most end surface of the distal portion of the flexible catheter and deflecting the distal portion about a center point, the elbow bend projecting the radially curved portion laterally away from the longitudinal axis, wherein a majority of the pre-formed compound curve is disposed distally of a distal end of the proximal portion of the flexible catheter.

11. The catheter assembly according to claim 10, further comprising a control handle disposed at the proximal portion of the flexible catheter and configured to advance and rotate the flexible catheter within the patient's airways.

12. The catheter assembly according to claim 10, wherein the pre-formed compound curve includes a first end connected to the distal end of the proximal portion of the flexible catheter.

13. The catheter assembly according to claim 10, wherein the elbow bend has a radius of curvature that is different than a radius of curvature of the radially curved portion.

14. The catheter assembly according to claim 10, wherein the distal-most end surface of the distal portion of the flexible catheter faces the longitudinal axis defined by the proximal portion of the flexible catheter.

15. A catheter assembly for navigation within a patient's airways, comprising:
- a flexible catheter defining a lumen and including a proximal portion and a distal portion, the distal portion having a distal end defining an opening that is in communication with the lumen and configured to allow passage of an instrument out of the flexible catheter; and
- a pre-formed compound curve formed on the distal portion of the flexible catheter and having a first end connected to a distal end of the proximal portion of the flexible catheter, the pre-formed compound curve including:
  - an elbow bend deflecting the distal portion of the flexible catheter from a longitudinal axis defined by the proximal portion of the flexible catheter; and
  - a radially curved portion extending from the elbow bend to a distal-most end surface of the distal portion of the flexible catheter and deflecting the distal portion about a center point, the elbow bend projecting the radially curved portion laterally away from the longitudinal axis, wherein the end surface of the distal portion of the flexible catheter faces the longitudinal axis.

16. The catheter assembly according to claim 15, wherein a majority of the pre-formed compound curve is disposed distally of the distal end of the proximal portion of the flexible catheter.

17. The catheter assembly according to claim 15, wherein the elbow bend has a radius of curvature that is different than a radius of curvature of the radially curved portion.

18. The catheter assembly according to claim 15, further comprising a control handle disposed at the proximal portion of the flexible catheter and configured to advance and rotate the flexible catheter within the patient's airways.

* * * * *